(12) United States Patent
Ye et al.

(10) Patent No.: US 7,538,881 B2
(45) Date of Patent: May 26, 2009

(54) FREQUENCY COMB CAVITY ENHANCED SPECTROSCOPY

(75) Inventors: Jun Ye, Louisville, CO (US); Michael J. Thorpe, Boulder, CO (US); Kevin Moll, Boulder, CO (US); R. Jason Jones, Tucson, AZ (US)

(73) Assignee: The Regents of the University of Colorado, a body Corporate, Denver, CO (US)

( * ) Notice: Subject to any disclaimer, the term of this patent is extended or adjusted under 35 U.S.C. 154(b) by 154 days.

(21) Appl. No.: 11/707,550

(22) Filed: Feb. 16, 2007

(65) Prior Publication Data
US 2008/0074660 A1 Mar. 27, 2008

Related U.S. Application Data

(60) Provisional application No. 60/774,820, filed on Feb. 17, 2006.

(51) Int. Cl.
*G01B 9/02* (2006.01)
*G01J 3/45* (2006.01)
(52) U.S. Cl. .................................... 356/454
(58) Field of Classification Search ............... 356/454, 356/480, 519
See application file for complete search history.

(56) References Cited

U.S. PATENT DOCUMENTS 7,099,015 B2 * 8/2006 Melnyk ...................... 356/480

2003/0189711 A1 * 10/2003 Orr et al. .................... 356/484

OTHER PUBLICATIONS

Ye, Jun et al., Ultrasenstive detections in atomic and molecular physics: demonstration in molecular overtone spectroscopy, Journal of Optical Society of America B-Opt. Phys., Jan. 1998, pp. 6-15, vol. 15, No. 1.
Gherman, T. et al., Mode-locked cavity-enhanced absorption spectroscopy, Optics Express, Sep. 23, 2002, pp. 1033-1042, vol. 10, No. 19.
Crosson, E.R. et al, Pulse stacked cavity ring-down spectroscopy, Review of Scientific Instruments, Jan. 1999, pp. 4-10, vol. 70., No. 1.
He, Y. et al., Rapid measurement of cavity ringdown absorption spectra with a swept-frequency laser, Applied Physics B., Oct. 11, 2004, pp. 941-945, vol. 79.
Cundiff, S. et al., Colloquium: Femtosecond optical frequency combs, Reviews of Modern Physics, Jan. 2003, pp. 325-342, vol. 75.

(Continued)

*Primary Examiner*—Michael A Lyons
(74) *Attorney, Agent, or Firm*—Jennifer Bales; Macheledt Bales & Heldmiller LLP (57) ABSTRACT

Cavity enhanced spectroscopy efficiently couples a broadband optical frequency comb to a high finesse optical cavity inside which a sample test gas is placed. The output of the optical cavity is a multiplicity of channels of data resulting from the differential absorption of light at various of the comb frequencies. The device can operate in a ringdown mode or a non-ringdown enhanced absorption spectroscopy mode. Careful measurement and control of cavity dispersion and comb spacing are part of the coupling process. Several dispersive detection methods adapted to detecting the multiplicity of channels are provided.

24 Claims, 6 Drawing Sheets

OTHER PUBLICATIONS

Jones, R. Jason et al., Precision stabilization of femtosecond lasers to high-finesse optical cavities, Physical Review A, Jan. 21, 2004, pp. 051803 1-4, vol. 69.

Thorpe, M. et al., Precise measurements of optical cavity dispersion and mirror coating properties via femtosecond combs, Optics Express, Feb. 7, 2005, pp. 882-888, vol. 13, No. 3.

Jones, R. Jason et al., Femtosecond pulse amplification by coherent addition in a passive optical cavity, Optics Letters, Oct. 15, 2002, pp. 1848-1850, vol. 27, No. 20.

Vega, A. et al., Generalized grating equation for virtually-imaged phased-array spectral dispersers, Applied Optics, Jul. 10, 2003, pp. 4152-4155, vol. 42, No. 20.

Scherer, J. et al., Broadband ringdown spectral photography, Applied Optics, Dec. 20, 2001, pp. 6725-6732, vol. 40, No. 36.

Thorpe, M. et al., Broadband cavity ringdown spectroscopy for sensitive and rapid molecular detection, Science, Mar. 17, 2006, pp. 1595-1599, vol. 311.

* cited by examiner

FREQUENCY COMB CAVITY ENHANCED SPECTROSCOPY

PRIORITY

This application claims the benefit of U.S. Provisional Patent Application Nos. 60/774,820, filed Feb. 17, 2006 and incorporates it herein by reference.

GOVERNMENT SUPPORT

The present invention was made with the support of the U.S. government which may have certain right in this invention. See Air Force Office of Scientific Research (AFOSR), contract # F49620-03-1-0415, Office of Naval Research (ONR), contract # N00014-02-1-0714, National Institute of Standards and Technology (NIST), grant # NBRAH90H027, National Institute of Standards and Technology (NIST), grant # 70NANB5H1108.

BACKGROUND OF THE INVENTION

1. Field of the Invention

The present invention relates to broad bandwidth trace detection apparatus and techniques. More specifically, the present invention relates to highly sensitive real-time spectroscopy.

2. Problems in the Art

Over the past century enormous effort has been invested in the development of spectroscopic methods for monitoring and making quantitative measurements of the physical world. As a result modern, spectroscopic approaches represent some of the most precise and widely used measurement tools. Frequency measurements such as the 1 S to 2 S transition in hydrogen (1) are rapidly improving, providing ever more rigorous tests of fundamental theories and creating insights for more in-depth investigations of atomic structure. Similarly, new and more powerful spectroscopic techniques are continually in demand for challenging chemical physics applications such as recording the high overtone spectrum of $H_3^+$ (2) or observing the isomerization process in vinylideneacetylene (3). Spectroscopy capable of such measurements is essential for the verification and further development of molecular theory. More practical applications of spectroscopy such as the real-time detection of trace amounts of molecular species are in demand in varying contexts. Such applications range from a security staging area in an airport for detection of trace amounts of molecules found in explosives or biologically hazardous materials to a doctor's office where a patient's breath could be analyzed as a non-intrusive method for monitoring diseases such as renal failure (4) and cystic fibrosis (5). Spectroscopic systems capable of making the next generation of atomic and molecular measurements will require: i) A large spectral bandwidth allowing for the observation of global energy level structure of many different atomic and molecular species; ii) High spectral resolution for the identification and quantitative analysis of individual spectral features; iii) High sensitivity for detection of trace amounts of atoms or molecules and for recovery of weak spectral features; iv) A fast spectral acquisition time, which takes advantage of high sensitivity, for the observation of spectral changes due to changing environmental conditions, leading to the study of dynamics.

Unfortunately, the characteristics of a good spectroscopic system are often in competition with each other. For example, designing a system with a large spectral bandwidth and high resolution (or high sensitivity) is fundamentally challenging due to the difficulty of selecting a narrow spectral band from a broad-spectrum source. As a result of such trade-offs, modern spectroscopic methods which are designed to meet two or three of the desired system characteristics with excellent performance will function poorly in the remaining areas. Single pass absorption techniques such as Fourier transform infrared (FTIR) (6) and wavelength agile methods (7) do an excellent job of providing large bandwidths up to several hundreds of nanometers and achieve remarkably fast acquisition times by recording entire spectra in microseconds. However, these methods offer sensitivities that are many orders of magnitude too low for applications involving trace detection or observation of weak spectral features. Both of these techniques are capable of achieving high resolution, but at a cost. For FTIR, the cost of high resolution is prolonged acquisition times. For wavelength agile techniques, high resolution is attained only if the spectral bandwidth is drastically decreased. Contrarily, cavity enhanced techniques such as noise immune cavity enhanced optical heterodyne molecular spectroscopy (NICE-OHMS) (8), and cavity ringdown spectroscopy (CRDS) (9) offer incredibly high sensitivities of 1 part in $10^{10}$ and beyond at 1 s averaging time and can provide high resolution, but these methods are generally limited to small spectral bandwidths of a few nanometers. Newer approaches to cavity enhanced spectroscopy have been directed at increasing the spectral bandwidth and reducing the acquisition time (10, 11, 12, 13). Such efforts have demonstrated large bandwidths of up to 50 nm with an acquisition time of 2 s (12), and fast acquisition times of 1 ms for a bandwidth of 0.5 nm (13). However, these methods have yet to demonstrate tens of nanometers of spectral bandwidth at millisecond acquisition times.

There remains a need in the art for spectroscopic methods and apparatus that address all of the mentioned system characteristics, yielding a powerful combination of bandwidth, sensitivity, resolution, and acquisition speed unmatched by any existing approaches.

REFERENCES

1. Th. Udem, R. Holzwarth, T. W. Haensch, *Nature* 416, 233 (2002).
2. J. L. Gottfried, B. J. McCall, T. Oka, *J. Chem. Phys.* 118, 10890 (2003).
3. M. P. Jacobson, R. W. Field, *J. Phys. Chem.* 104, 3073-3086 (2000). M. J. Jensen, U. V. Pedersen, L. H. Andersen, *Phys. Rev. Lett.* 84, 1128 (2000).
4. L. R. Narasimhan, W. Goodman, C. K. N. Patel, *Proc. Nat'l. Acad. Sci. U.S.A.* 98, 4617 (2001).
5. S. A. Kharitonov, P. J. Barnes, *Am. J. Respir. Crit. Care Med.* 163, 1693 (2001).
6. F. Keilmann, C. Gohle, R. Holzwarth, *Opt. Lett.* 29, 1542 (2004).
7. S. T. Sanders et al., *Optics and Photonics News* 16, 36 (2005).
8. J. Ye, L. S. Ma, J. L. Hall, *J. Opt. Soc. Am. B-Opt. Phys.* 15, 6 (1998).
9. J. Ye, J. L. Hall, *Phys. Rev. A* 61, 061802 (2000).
10. T. Gherman, D. Romanini, *Opt. Express* 10, 1033 (2002).
11. E. R. Crosson et al., *Rev. Sci. Instrum.* 70, 4 (1999).
12. Y. He, B. J. Orr, *Appl. Phys. B* 79, 941 (2004).
13. I. Debecker, A. K. Mohamed, D. Romanini, *Opt. Express* 13, 2906 (2005).
14. S. T. Cundiff, J. Ye, *Rev. Mod. Phys.* 75, 325 (2003).
15. R. J. Jones, I. Thomann, J. Ye, *Phys. Rev. A* 69, 051803 (2004).

16. M. J. Thorpe, R. J. Jones, K. D. Moll, J. Ye, R. Lalezari, *Opt. Express* 13, 882 (2005).
17. R. J. Jones, J. Ye, *Opt. Lett.* 27, 1848 (2002).
18. Mention of product names is for technical communication only and does not represent the endorsement by the authors.
19. A. Vega, A. M. Weiner, C. Lin, *Appl. Opt.* 42, 4152 (2003).
20. J. J. Scherer et al., *Appl. Opt.* 40, 6725 (2001).
21. J. Ye, *Ph. D. Dissertation, University of Colorado* (1997).
22. F. Herregodts, D. Hurtmans, J. Vander Auwera, M. Herman, *Chem. Phys. Lett.* 316, 460 (2000).
23. HITRAN molecular database 2005.
24. C. I. Sukenik, H. C. Busch, *Rev. Sci. Instrum.* 73, 493 (2001).
25. M. J. Thorpe, K. D. Moll, R. J. Jones, B. Safdi, and J. Ye, *Science*, 311, 1595-1599 (2006).
26. We thank E. Hudson for technical discussions, S. Cundiff and R. McLeod for equipment loans. The research work at JILA is supported by AFOSR, ONR, NASA, NIST, and NSF. M. J. Thorpe thanks NSF-IGERT and the Univ. of Colorado Optical Science and Engineering Program for financial support.

SUMMARY OF THE INVENTION

An object of the present invention is to provide spectroscopic methods and apparatus yielding a powerful combination of bandwidth, sensitivity, resolution, and acquisition speed unmatched by any existing approaches. This is accomplished by efficiently coupling a broadband frequency comb into a high finesse optical cavity, creating simultaneous detection channels of on the order of hundreds of thousands individual cavity modes.

Apparatus according to the present invention for performing enhanced spectroscopy on a test sample on many channels of data at once comprises means for providing a broadband optical frequency comb such as a mode locked laser, a high finesse, low-dispersion optical cavity within which the test sample is stored, means for coupling the optical frequency comb to the cavity, and means for measuring cavity transmission at a multiplicity of frequencies, generally including an optical detector.

A processor for determines absorption within the cavity at the multiplicity of frequencies from the measured cavity transmission and determines the composition of the test sample based upon the determined absorption.

The means for coupling comprises means for measuring the wavelength dependent frequency spacing of cavity modes due to dispersion and means for making adjustments based on the wavelength dependent frequency spacing of cavity modes in order to match comb frequencies to cavity modes. For example, the means for measuring might include apparatus for detuning the frequency comb from the cavity modes, varying the repetition rate, and monitoring the spectrum of light transmitted from the cavity. And the means for making adjustments might vary the repetition rate and offset of the comb, or alternatively adjust the cavity length and vary at least one of either the sample composition or the sample pressure. The means for making adjustments might further include an electronic servo for maintaining the match between comb frequencies and cavity modes.

The means for measuring cavity transmission might comprise an element for spatially separating wavelengths in the transmission and a photodiode array configured to detect the intensities of separated wavelengths and generate voltages based upon the detected intensities. This embodiment is particularly useful in ringdown mode and would further comprise means for interrupting the optical frequency comb periodically and means for comparing the generated voltages over time to a series of descending voltage thresholds, wherein the voltage thresholds are exponentially spaced in order to reduce computations needed to determine decay rate at the wavelengths.

Alternatively the means for measuring cavity transmission might comprise means for sweeping the comb frequencies over a preselected period of time such that a selected group of comb frequencies at a time couples to the cavity, and means for measuring the intensity of each transmitted selected group of comb frequencies in turn. The selected group of comb frequencies might comprise between 1 and 10,000 comb frequencies.

The invention provides a spectral bandwidth of up to several hundred nanometers, achieving a spectral resolution of 0.01 cm$^{-1}$. In a ringdown configuration, integrated absorption sensitivity of 1×10$^{-8}$ at 1 s is achieved and acquisition time of 1.4 ms is realized for a spectral window of more than 3 Terahertz. In a cavity enhanced absorption configuration a similar integrated absorption sensitivity of 1×10$^{-8}$ at 1 s is achieved, but the acquisition time is limited to the CCD frame rate of 60 Hz. In principle, this acquisition time is limited only by the actual cavity ringdown time (several microseconds). The novel capabilities of this spectroscopic system have been demonstrated via measurements of several atomic and molecular species (Ar, $C_2H_2$, $O_2$, $H_2O$, $NH_3$), revealing quantitative information about the gas concentrations, linewidths, collision rates, temperatures, and plasma dynamics.

BRIEF DESCRIPTION OF THE DRAWINGS

FIGS. 1A and 1B (Background Art) are diagrams illustrating coupling pulses from a mode-locked laser into a high finesse optical cavity.

FIGS. 2A, 2B, 2C, and 2D illustrate measurement and control of dispersion of the optical cavity in the process of the present invention.

FIGS. 3A, 3B and 3C show a block diagram of a preferred embodiment of the present invention; wherein

FIGS. 5A and 5B illustrate a second method of dispersive detection.

DETAILED DESCRIPTION OF THE PREFERRED EMBODIMENTS

Some of the abbreviations used in the following Description are defined below for convenience.

Mode-locked laser—A laser that uses a passive or active effect to create a constant phase relationship among many modes (frequencies) that are all lasing simultaneously. The output of such a laser is a train of pulses with a fixed separation in the time domain and a comb-like structure in the frequency domain.

$f_{rep}$—An abbreviation for the repetition frequency of a mode-locked laser. It denotes the rate at which pulses are emitted from the mode-locked laser.

$f_o$—An abbreviation for the carrier envelope offset frequency of the frequency comb emitted by the mode-locked laser. This frequency can take on values between 0-$f_{rep}$.

frequency comb—The regularly spaced set of frequencies emitted by a mode-locked laser. These frequencies are written mathematically as $v_n = n\, f_{rep} + f_o$. The center frequency of the comb and the number of modes that are present depend on a wide variety of factors including the lasing material, the laser cavity length, dispersion control, and whether spectral broadening or shifting techniques are employed.

FSR—An abbreviation for free spectral range of the high finesse cavity which refers to the wavelength dependent spacing of the resonant modes of the cavity.

Finesse—A measure of the quality of an optical resonator defined as Finesse=FSR/$\delta v$, where $\delta v$ is the linewidth of the cavity modes.

High finesse optical cavity—A resonator for optical frequencies. Usually constructed from two low-loss, low-dispersion mirrors; this is the chamber used for molecular detection.

Figure 1A:
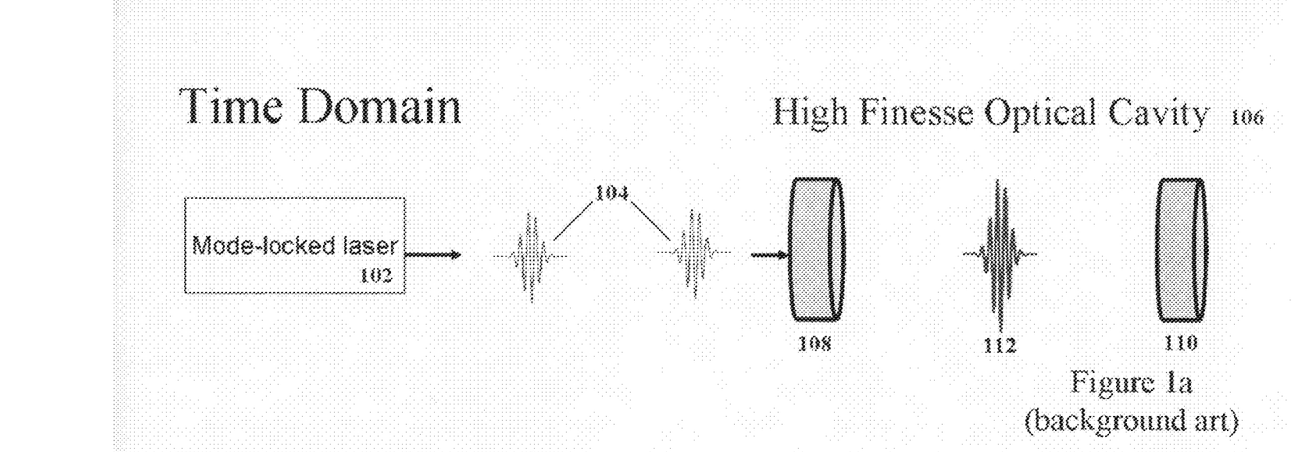
FIG. 1A is a flow diagram illustrating the process in the time domain.
Figure 1B:
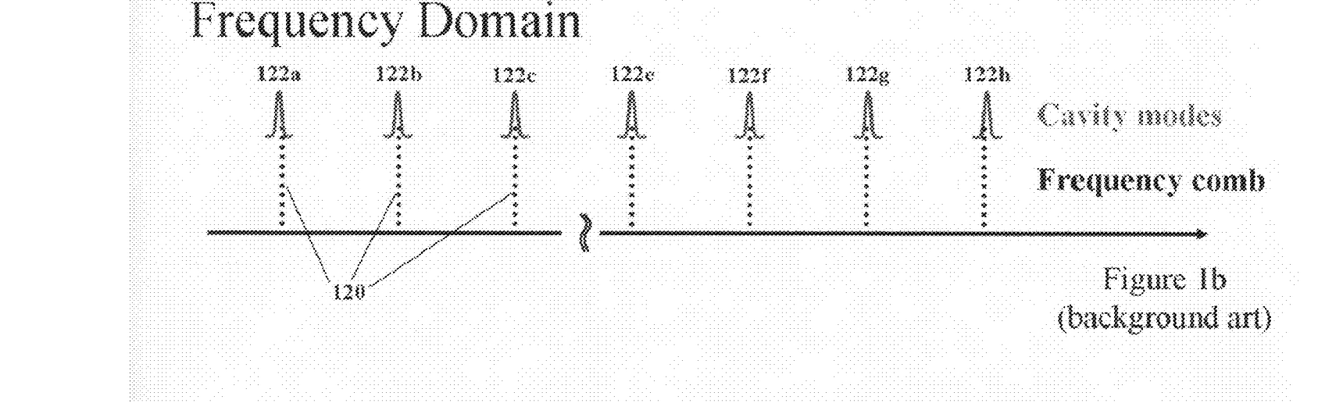
FIG. 1B illustrates cavity modes matched to comb frequencies in the frequency domain.

FIGS. 1A and 1B (Background Art) are diagrams illustrating the process of coupling pulses from a mode-locked laser 102 into a high finesse optical cavity 106. In the time domain, this can be seen as coherently adding many laser pulses inside the cavity. In the frequency domain, this corresponds to matching the comb frequencies ($V_n = n\, f_{rep} + f_o$) to the resonant frequencies of the cavity.

FIG. 1A is a flow diagram illustrating the process in the time domain. FIG. 1B illustrates cavity modes 122 matched to comb frequencies 120 in the frequency domain.

Figures 3A, 3B, 3C:
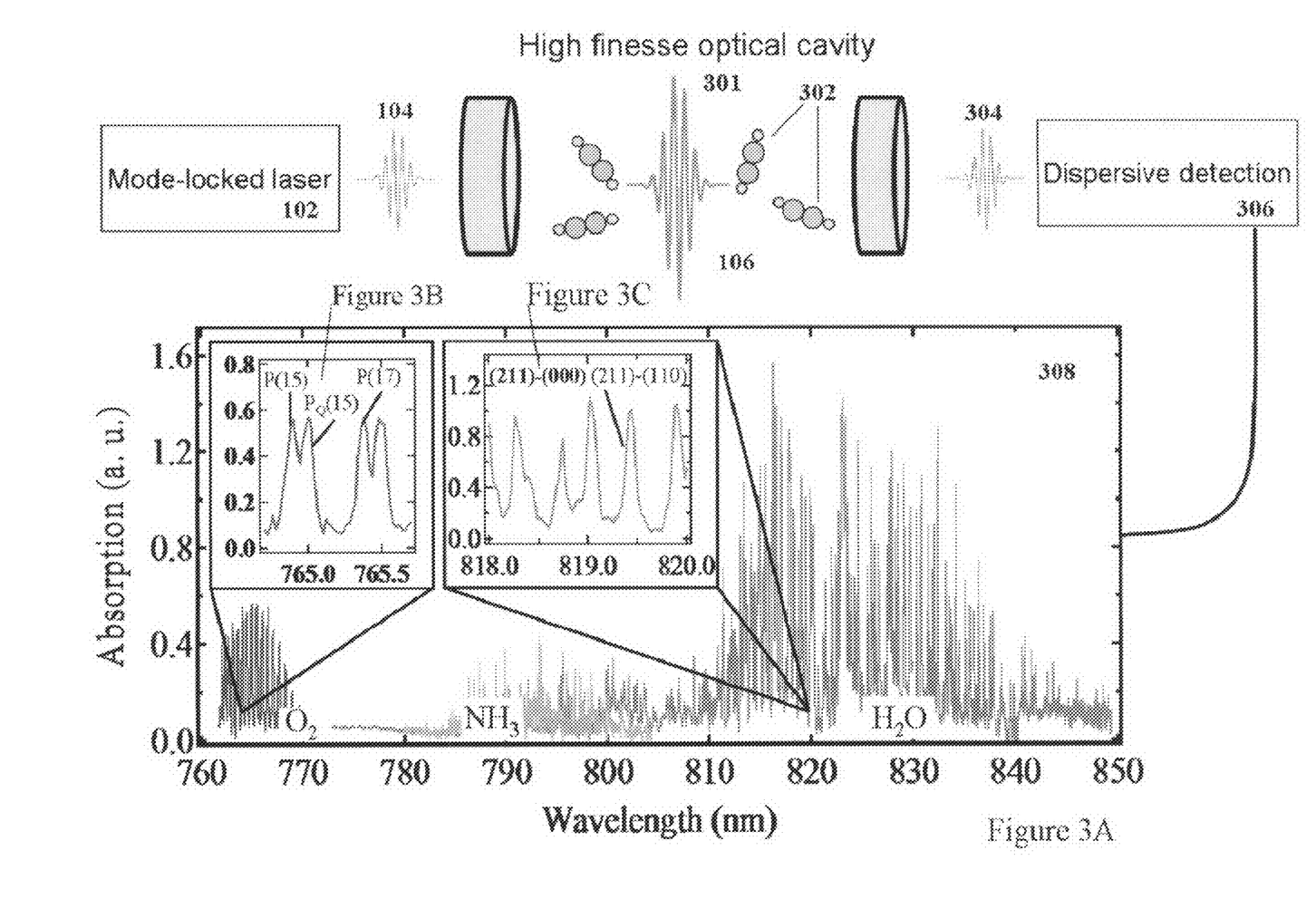
FIG. 3A shows the spectroscopy process.
FIG.3B shows a first portion of the detected spectrum and FIG. 3C shows a second portion of the detected spectrum.

Mode locked laser 102 generates pulses 104, which can be represented in the frequency domain as many comb components 120. Pulses 104 are coupled into high finesse optical cavity 106, comprising end mirrors 108 and 110. Each pulse propagates in cavity 106 for many round-trips, interacting with any test sample over an extended effective path length that is given by $l_{eff} = (2 \times \text{Finesse} \times l)/\pi$, where l is the distance between the two end mirrors. End mirrors 108 and 110 are highly reflective, but allow a small portion of the intra-cavity beam to exit during each reflection. The light exiting the cavity is affected by the test sample such that certain frequencies are absorbed (as shown in FIG. 3A). Analyzing the absorption at the different light frequencies allows determination of the composition of the test sample (this is the principle behind spectroscopy in general).

FIG. 1B illustrates the coupling of pulses 104 into cavity 106 in the frequency domain. Frequency comb 120 is the multiplicity of frequencies generated by laser 102. Those skilled in the art of mode-locked lasers will appreciate that many equally spaced frequencies are generated by such lasers, for example via a nonlinear Kerr effect within the laser gain medium.

For the comb components 120 to be coupled into cavity 106, they must have the same frequencies as the cavity modes. Since the pulses reflect back and forth many times, only those frequencies which are constructively reinforced in the cavity will survive and be transmitted in output pulses. In other words, each frequency must fit within the cavity with an integer number of wavelengths or it will be extinguished. The higher the finesse of the cavity the narrower the cavity modes will be, and the closer the frequency match must be.

Returning to FIG. 1B, the example illustrated shows some of the comb frequencies, but not all, matched up to cavity modes. Thus, the comb frequencies corresponding to cavity modes 122c, 122e and 122f will couple efficiently to the cavity (the broken frequency axis indicates that many comb components are not shown in the figure). Frequencies 122b and 122g will experience poor coupling with the cavity resulting in a highly attenuated transmission signal. These mismatches arise from the fact that FSR is not a constant across the laser spectrum due to the presence of dispersion inside the cavity 106.

FIGS. 1A and 1B illustrate a difficulty which had to be overcome in developing the present invention. Matching the cavity modes to the frequency comb is a difficult task, especially once a test sample is added to cavity 106. The dispersion caused by mirrors 108, 110 is constant and predictable, but the dispersion caused by the test sample is harder to accommodate. The process of adjusting for the dispersion of both the cavity and the sample is illustrated in FIG. 2A-2D.

Figure 2A:
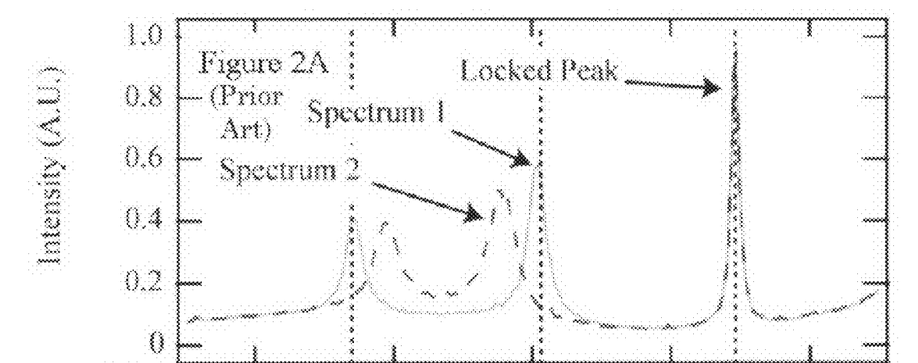
FIG. 2A shows intensity spectrum of light transmitted from the cavity at two different repetition frequencies.
Figure 2B:
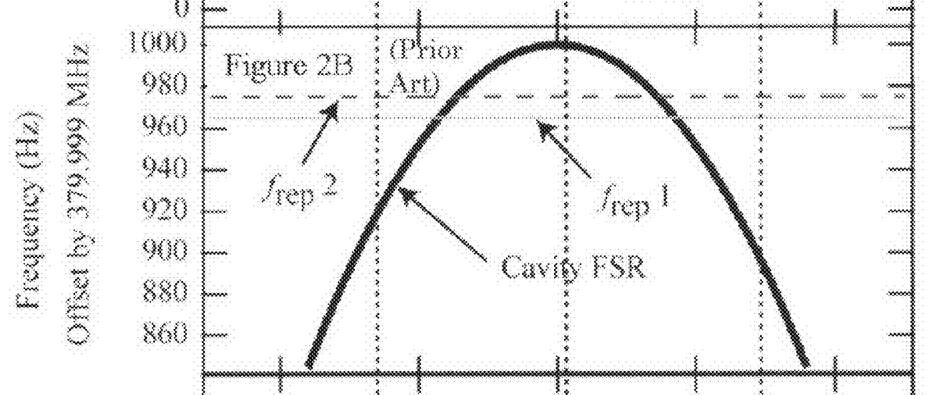
FIG. 2B shows the variation of cavity FSR due to dispersion and two different selections of cavity resonance modes under two different repetition frequencies.
Figure 2C:
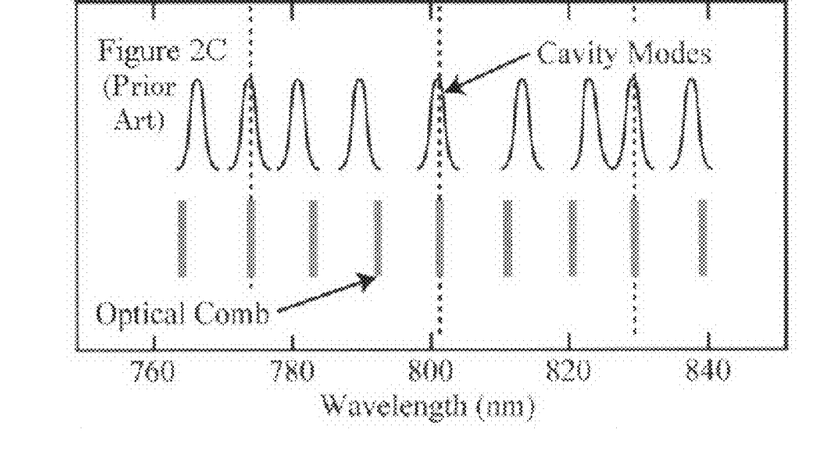
FIG. 2C shows how matching of cavity modes to comb frequencies produces the spectra of FIG. 2A.

FIGS. 2A, 2B, 2C, and 2D illustrate measurement and control of dispersion in cavity 106. While the frequency spacing of the comb modes is constant as a function of optical frequency, the resonant modes of the high finesse cavity are subject to dispersion, which results in a wavelength-dependent frequency spacing of the cavity modes, i.e., a wavelength-dependent FSR. The effect of dispersion is to limit the spectral bandwidth of the frequency comb that can be coupled into the optical cavity, reducing the number of channels of data which can eventually be derived. To mitigate the effects of dispersion, the dispersion of the high finesse optical cavity is first measured to high precision. This measurement is accomplished by locking the frequency comb to the optical cavity at one particular choice of an optical frequency, under the condition that the cavity FSR is actually detuned from the laser $f_{rep}$. As one changes $f_{rep}$, the comb modes are then expanded and contracted about the locking point and the spectrum of light transmitted from the cavity is monitored. This process is illustrated in FIGS. 2A, 2B, and 2C. By recording the transmission spectrum under various choices of $f_{rep}$, the cavity dispersion is determined. Once the dispersion is measured, various techniques can be used to minimize the cavity dispersion, such as the use of special mirrors with tailored dispersion properties, including possible use of negative dispersion mirrors, as well as adjustments to the concentration of the test sample gas, and the pressure of a buffer gas. In particular, precise knowledge of the intra-cavity dispersion is essential for time domain detection of the cavity transmission shown in FIG. 5.

FIG. 2A shows intensity of transmitted light spectra at two different repetition frequencies, $f_{rep}1$ and $f_{rep}2$, shown in FIG. 2B along with the cavity FSR. The repetition frequency is the rate at which pulses are emitted by the mode-locked laser 102. The repetition frequency defines the frequency comb spacing, which does not vary with wavelength in the frequency domain. Hence the repetition frequencies are shown as straight lines in FIG. 2B. The FSR of the cavity exhibits frequency dependence also shown in FIG. 2B Neither choice of repetition frequency shown in FIG. 2B allows many of the comb frequencies to be coupled into the cavity. This is because not many comb frequencies are aligned with cavity modes, as illustrated in FIG. 2C. FIG. 2C shows the comb/mode alignment achieved at $f_{rep}1$. Only the modes/frequencies centered about 774 nm, 801 nm and 829 nm are aligned, and hence only those frequencies are present in cavity transmission, as shown in FIG. 2A. In general, the present invention operates best when a broad range of comb frequencies are coupled into the cavity. This can only be accomplished by minimizing the cavity dispersion and adjusting the $f_{rep}$ of the laser to match the cavity FSR. Also, the $f_o$ of the laser must be adjusted such that the comb frequencies match the cavity resonances.

Figure 2D:
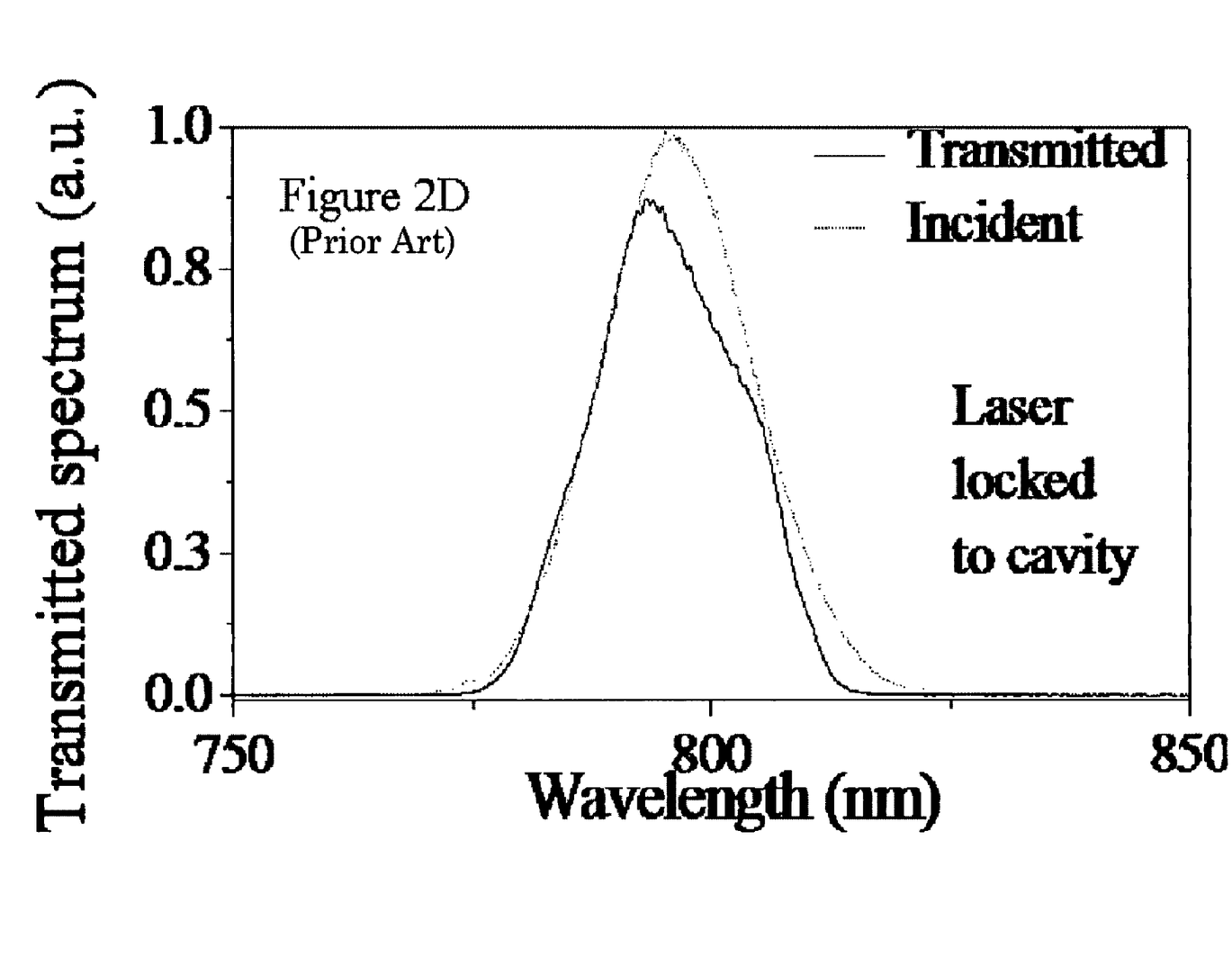
FIG. 2D shows the actually measured transmitted spectrum when the laser is locked to the cavity.

FIG. 2D shows the transmitted spectrum when the laser 102 is locked to the cavity 106. Now all of the comb frequencies 120 over a broad range of wavelengths align well to the cavity modes 122, and all will propagate and show up in the output pulses, after interacting with the test sample and being differentially absorbed. In order to achieve the results shown in FIG. 2D, either the comb frequencies or the cavity modes must be adjusted such that they properly align at wavelengths of interest. In the present invention, this is generally achieved by adjusting $f_{rep}$ and $f_o$ of laser 102. This can be done with sufficient accuracy by adjusting the cavity length and the pump laser power in laser 102.

FIG. 3A, 3B and 3C show a block diagram of a preferred embodiment of the present invention; wherein FIG. 3A shows the spectroscopy process, FIG. 3B shows a first portion of the detected spectrum and FIG. 3C shows a second portion of the detected spectrum. Mode-locked laser 102 generates pulses 104 comprising a multiplicity of frequencies forming a frequency comb. Pulses 104 are coupled into high finesse optical cavity 106, as described in conjunction with FIGS. 2A-D. Optical cavity 106 contains a gas test sample 302 to be detected.

Incident pulses 104 are coupled into the cavity. Intracavity pulses 301 reflect back and forth within cavity 106 many times (e.g. 10,000 times or more) and hence interact with test sample 302 for a sufficiently long period of time to allow comb frequencies to be differentially absorbed according to the composition of test sample 302. Output pulses 304 hence contain information about the composition of test sample 302.

In order to accurately determine the composition of test sample 302, the absorption of light at each frequency must be determined. Hence, the output pulses 304 must be fanned out in frequency (such that frequencies are spatially separated) and then each frequency must be detected. These two functions (dispersion and detection) are performed in dispersive detection block 306.

FIGS. 4 and 5A-5D illustrate two dispersive detection schemes. Whatever the scheme, the output of dispersive detection block 306 designates the absorption of light in output pulse 304 at each of many frequencies. Display 308 shows how such data might be displayed. FIG. 3B is a blown up portion of the display, in the frequency region indicating oxygen in the test sample. FIG. 3C is a blown up portion of the display in the wavelength region indicating the presence of water.

Figure 4:
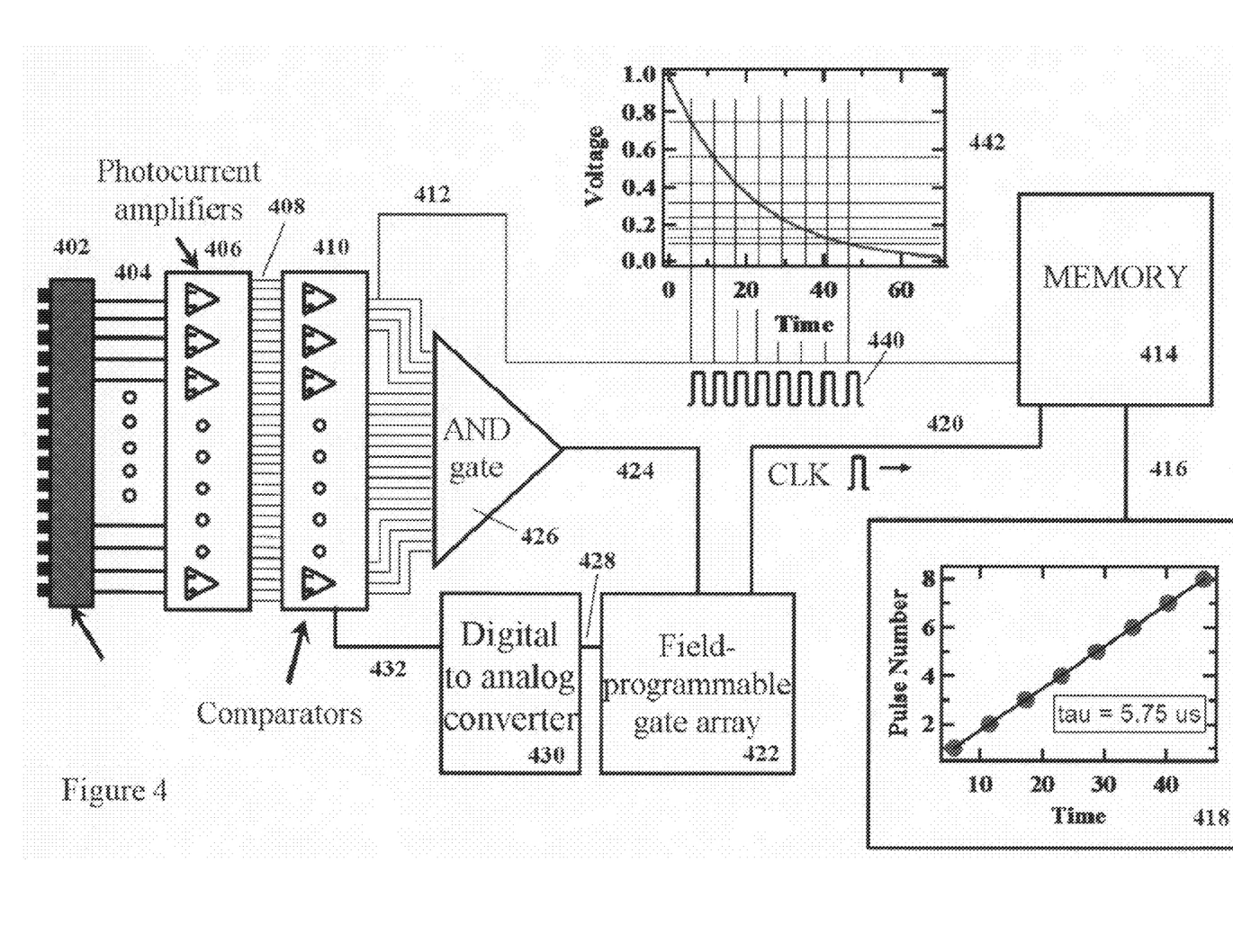
FIG. 4 is a schematic diagram showing a first method of dispersive detection. A spectrometer, such as a grating or virtually imaged phased-array (VIPA) spectrometer, is used to spatially disperse the beam transmitted from the cavity. A detector array is then used to detect the dispersed light. This detector can be a 1 D or 2 D array. The method in FIG. 4 describes how ringdown signals can be simultaneously sampled from each of the detector array elements.

FIG. 4 is a schematic diagram showing a first method of dispersive detection, wherein parallel sampling of multiple channels is accomplished using a photodiode array. The embodiment of FIG. 4 is particularly useful in cavity ringdown scenarios, wherein cavity 106 is allowed to fill up with light, and then the input from laser 102 is switched off. The output signal 304 will decay with time, and the rate at which the output at each frequency decays is indicative of how much light is being absorbed in the sample at that particular frequency. The cavity ringdown method has the advantage of eliminating variations in the intensity of laser 102 as a source of noise and error. The difficulty in using cavity ringdown is that the decay occurs quickly, so many measurements must be made in a very short period of time. The embodiment of FIG. 4 can operate at the requisite clock rate to accomplish ringdown spectroscopy for the many channels of data provided by the present invention.

The embodiment of FIG. 4 is configured to substantially reduce the computational load of determining the decay rates of many channels of data. The spectrum of signal 304 is spread out spatially by a device (not shown) such as a prism, a grating, or a VIPA spectrometer, and is generally imaged onto the detector array using a lens. Photo-diode detector array 402 then detects the intensity of light at a large number of frequencies. The voltage signals 404 provided by array 402 are amplified in photocurrent amplifiers 406 to generate amplified signals 408. Comparators 410 generate an electrical pulse that is recorded by the memory every time a decay signal crosses the reference voltage. The digital to analog converter generates reference voltages for the comparators that are shown in graph 442. Switching between these reference voltages is controlled by the FPGA 422. Finally, AND gate and D-flip-flop functionality 426 (usually embedded within the FPGA) cause the reference voltage for a block of comparators to switch to the next lowest voltage after each channel in the block has crossed the current reference voltage. A "block" of channels usually corresponds to 15-30 neighboring detector channels that all use the same reference voltages. A filter mask can be implemented within the FPGA to measure whether the slowest decaying channel within a block crosses the $n^{th}$ reference voltage before the fastest decaying signal crosses the $(n+1)^{th}$ reference voltage. If this doesn't happen for all reference voltages, the slowly decaying channels can be masked out and the measurement can be taken again to recover the decay time of the fast channels.

The analog electronic signal of an individual frequency component after laser 102 has been turned off in a cavity ringdown configuration has the form:

$$V(t) = V_o \exp(-t/\tau);$$

Where V0 is the voltage when the laser is turned off, V(t) is the voltage at time t and $\tau$ is the decay time. Since the electronic signal is an exponential function, the embodiment of FIG. 4 measures the time interval instead of computing $\tau$ from the exponential signal.

$$\Delta t_{12} = \tau \log(V_1/V_2)$$

$\Delta t_{12}$ is the time interval between when $V(t)=V_1$ and when $V(t)=V_2$. Since $\Delta t_{12}$ depends on the ratio of $V_1/V_2$, the ratio is deliberately kept constant as the device moves through successive voltage thresholds, to keep $\Delta t$ constant. This is shown in block 442, where a number of thresholds are shown as horizontal lines, and the spacing between the thresholds decreases exponentially. Thus, $\Delta t$ is essentially constant as the pulse decays (as shown by the vertical lines in block 442), and results in a linear decay signal 412 recorded by memory 414. Memory 414 is operated via a clock signal 420 from the FPGA 422 that defines the arrival time of each decay pulse in signal 412. τ is then determined from Δt data 416 as shown in block 418. Comparator block 410 compares each voltage 408 to a threshold voltage 432. Thus, when each signal has passed the threshold, AND gate 426 transmits a signal 424 to field programmable gate array 422, which sends signal 428 to the DAC 430 to provide the next threshold voltage for comparator block 410. As stated previously, AND gate 426 and other digital logic are usually embedded within FPGA 422.

While a single AND gate and DAC are shown in FIG. 4, the design can be modular, so that a separate AND gate and DAC are used for blocks of channels. Then, only the voltages in that block need to cross a threshold to trigger a new threshold voltage. Generally, $V_0$ and τ are approximately equal for neighboring channels, so it is usually safe to wait until the voltages on all of the channels fall below the reference voltage. If this is not the case, intelligent masking is used to determine voltage decay rates by ignoring troublesome channels (e.g. D flip flips determine what signals appear on the AND gate) while taking successive measurements. This logic is not shown but will be well understood to those in the field. The necessary digital logic (timers, shift registers, masking, etc.) may be easily implemented in an FPGA or ASIC.

Figure 5A:
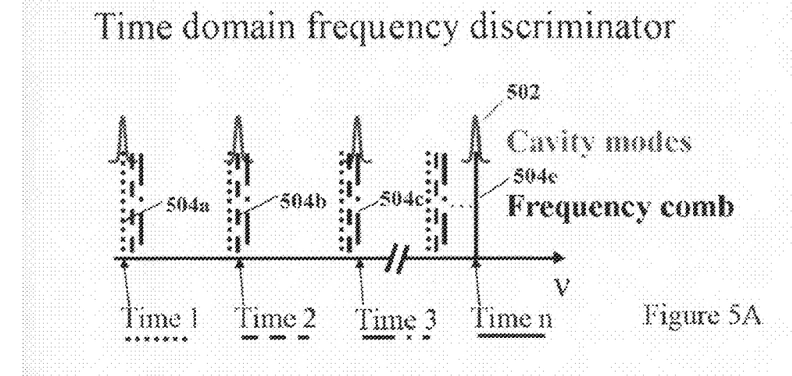
FIG. 5A illustrates a time domain frequency discriminator technique. This technique uses the cavity for both sensitivity enhancement and spectral dispersion as in a spectrometer. Individual comb components are successively tuned onto cavity modes with increasing frequencies, making one detection channel available at one particular time.
Figure 5B:
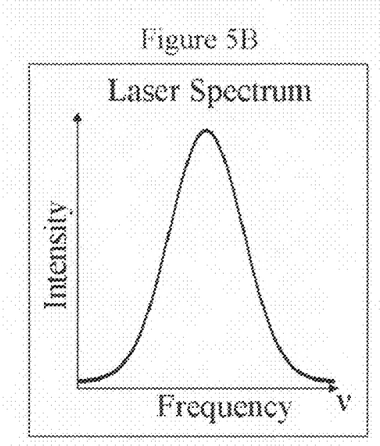
FIG. 5B illustrates the input laser spectrum.

FIGS. 5A and 5B illustrate a second method of dispersive detection, called time domain detection. Time domain detection may be performed in a ringdown device or in a cavity enhanced absorption spectroscopy device (i.e. non-ringdown). The idea behind time domain detection is that instead of coupling and analyzing the entire spectrum in signal 304 at the same time, only one color is transmitted at a time. The matching between the cavity modes and the comb frequencies is manipulated to allow only a very narrow band of frequencies (one or a few comb frequencies) to propagate through cavity 106. Then either the cavity or the laser is adjusted so that a different comb frequency propagates. The device walks through the frequencies, detecting the signal at each frequency, so that the entire is spectrum is sampled one comb component at a time successively.

This is done, for example, by purposely detuning the laser 102 repetition frequency $f_{rep}$ from the cavity 106 FSR. The laser $f_{rep}$ is then swept in a controlled manner such that successive frequencies come onto resonance with the cavity at successive times. The successive frequencies are then detected in cavity transmission, one at a time, by a single detector element 574. This technique is attractive due to the simplicity of using the cavity for the dispersive element as well as enhancement of the molecular absorption signal.

FIG. 5A illustrates the time domain frequency discriminator technique. Cavity modes 502 are shown at evenly spaced frequencies. Four different comb frequencies 504 are shown. In the embodiment of FIG. 5A, the optical comb frequencies are swept over a period of time, for example by varying the spacing of the mirrors (not shown) in laser 102.

At time 1, comb 504a matches one of the cavity modes 502, so that frequency 504a is propagated. Similarly, at time 2, 504b propagates, at time 3, frequency 504c propagates, and at time n, frequency 504e propagates. Thus the device has a data point for each comb frequency 504. In a ringdown configuration, this procedure would be performed with only one comb mode resonant with the cavity at a time. This mode is allowed to build up and then ringdown before the next mode is moved onto resonance. FIG. 5B shows intensity spectrum signal 104 from laser 102, before it enters cavity 106 and interacts with test sample 302. While the signal strength varies with frequency, it varies in a smooth and predictable manner. FIG. 5D shows signal 304 exiting cavity 106 after interacting with test sample 302. Now, light at some frequencies has been differentially absorbed by sample 302. Hence, the spectrum has holes in it showing where absorption has occurred. Note the spectrum signal is now displayed with respect to time.

Figure 5C:
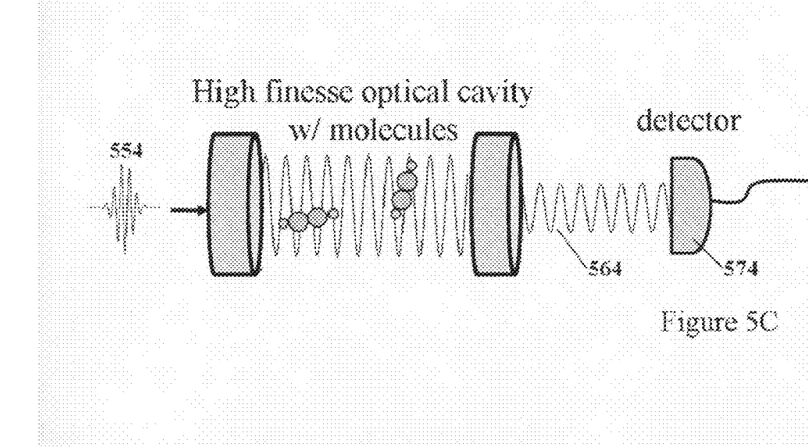
FIG. 5C is a schematic diagram showing absorption and detection in this scheme.
Figure 5D:
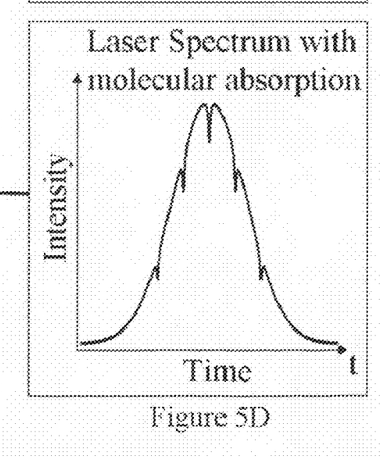
FIG. 5D shows the output spectrum, after the laser input has interacted with the test sample gas.

FIG. 5C is a schematic diagram showing absorption and detection in this scheme. Input signal 554 contains many colors, but is filtered by the cavity such that signal 564 contains only one (or alternatively a few) colors. Since the transmitted signal 564 comprises only one color of light at a time, signal 564 can be detected by a single detector 574.

Below is a detailed description of an experimental broadband cavity ringdown system according to the present invention, including laser and cavity parameters, detection schemes, and a description of the electronics used in the first realization this invention. This example is provided for illustrative purposes, and is not intended to limit the scope of the invention to the details of this embodiment.

The frequency structure of the comb is given by the relation $v_n = n f_{rep} + f_o$, where the integer n refers to the $n^{th}$ mode of the comb and $f_{rep}$ and $f_o$ refer to the repetition frequency and the carrier-offset frequency, respectively. For best results in matching this set of frequencies to a specific set of cavity modes it is necessary to independently control both $f_{rep}$ and $f_o$. Cavity modes and comb modes must have both the same spacing and the same offset so they overlap each other. For the Ti:sapphire oscillator used in this realization of the invention, such control is achieved with several piezo-electric (PZT) and picomotor actuators that adjust the length and dispersion of the laser cavity. Here, $f_{rep}$ is controlled by adjusting the cavity length using a combination of a picomotor for coarse adjustments and a PZT for fine adjustments. $f_o$ is controlled by tilting the high reflecting mirror in the dispersive arm of the Ti:Sapphire laser or by adjusting the power of a solid-state laser that pumps the mode-locked laser 102. When the comb frequencies are matched to the cavity modes, successive laser pulses add coherently inside of the cavity, resulting in enhanced intracavity intensities and ringdown signals.

A mode-locked Ti:sapphire laser generates a train of ~10 fs pulses with a repetition frequency ($f_{rep}$) of 380 MHz and an average power of 300 mW. This femtosecond optical frequency comb is passed through an acousto-optical modulator (AOM) and the $1^{st}$ order diffraction from the AOM is coupled into a high finesse (F=4500) optical cavity where the ringdown spectroscopy is performed). The free spectral range (FSR) of the cavity is 380 MHz, matching that of the optical comb such that translating the entire optical frequency comb would couple every single comb component into a respective cavity mode. The optical beam is spatially mode-matched to the cavity, and the cavity is also "impedance-matched" to ensure maximal input coupling of light. The optical comb is modulated about the cavity resonances by dithering the laser cavity length with a PZT. The dither frequency and voltage are chosen such that light builds up inside of the cavity for several microseconds prior to ringdown, allowing thousands of pulses to coherently add for each ringdown event. A photomultiplier tube (PMT) utilizes a small portion of the light transmitted from the cavity to detect when the light intensity inside of the cavity reaches a preset threshold. At this moment the AOM is switched off and the intensity in each cavity mode begins to decay (ringdown). The transmitted light from the cavity is passed through a ¼ meter monochromator [CVI model DK240] with a spectral resolution of 25 GHz, which is, of course, not the fundamental resolution limit of this detection scheme. In its simplest form, detection of ringdown events is performed by a single detector placed at the monochromator output image plane. In this case, the monochromator grating can be scanned to retrieve spectral information. In cases where fast, broadband spectral acquisition is desirable, a streak camera detection scheme is employed. A scanning mirror (Electro-Optical Products SC-10) is placed near the output image plane of the monochromator and is used to deflect the beam in the vertical direction, whereas the beam is spectrally dispersed in the horizontal direction. Spectrally dispersed wavelengths are recorded along the horizontal rows of pixels while the ringdown waveform in the time domain is recorded on the vertical columns of pixels. The scanning mirror is operated at 355 Hz allowing for the acquisition of a ringdown spectrum every 1.4 ms. The CCD is capable of exporting an entire ringdown image to the data acquisition computer every 300 μs so that the application of a faster scanner will result in increased acquisition rates. The CCD has 680 pixels in the horizontal dimension allowing for a single-shot acquisition of 15 nm of spectrum at 25 GHz resolution. By reducing the resolution larger spectral bandwidths can be recorded in a single shot. Finally, locking electronics are utilized which allow the laser repetition frequency to track the cavity FSR such that the optical comb remains resonant with the cavity for hours of uninterrupted spectral acquisition.

A more recent system that represents a more preferable embodiment of the invention is described below. A mode-locked erbium-doped fiber laser generates a 100 MHz frequency comb that is amplified and then spectrally broadened such that comb components between 1 μm and 2 μm are available for spectroscopy. This comb is coupled to a 1.5 meter long two mirror cavity with a peak finesse of F=30,000 at 1590 nm. The cavity maintains a high finesse for 1500 nm to 1700 nm.

As an alternative, a prism cavity is implemented to provide a comparable finesse over a much larger spectral bandwidth (i.e. F>30,000 from 1200 nm to 1800 nm). In the current system, light transmitted from the cavity is dispersed using a VIPA spectrometer. The dispersed light is imaged onto a Xenics 320 by 256 element InGaAs focal plane array. The f=20 cm lens used for the focusing allows 25 nm of spectrum to be recorded in a single shot. The 50 GHz FSR of the VIPA provides a resolution of 800 MHz. Therefore, a single VIPA image contains nearly 4000 channels of spectroscopic information, which can be recorded at the 60 Hz camera frame rate. A different spectral region can be explored by simply rotating the grating within the VIPA spectrometer. The overtone spectrum of $CO_2$ was used to measure both the resolution, mentioned above, and sensitivity of this spectrometer. A sensitivity of $1*10^{-10}$ cm$^{-1}$ at 1 second of averaging time has been achieved with a resolution of 800 MHz. Using this system, a wide variety of molecules including water, carbon monoxide, carbon dioxide, ammonia, methane, acetone, acetylene, and many others can be detected and investigated with high sensitivity and resolution.

While the exemplary preferred embodiments of the present invention are described herein with particularity, those skilled in the art will appreciate various changes, additions, and applications other than those specifically mentioned, which are within the spirit of this invention. For example, many methods may be used for spectrally dispersing and detecting the cavity transmission beam. The most traditional method is to use a grating monochromator with a single detector and read out the spectrum by rotating the grating. More sophisticated techniques involve the use of a CCD camera to record many channels in the monochromator output simultaneously. Yet another technique is to use a virtually imaged phase array (VIPA) spectrometer consisting of a VIPA etalon in one dimension and a grating in the other. This spectrometer allows the cavity transmission beam to be dispersed into two dimensions before being imaged onto a CCD camera. This technique is attractive for the very large number of channels that can be recorded in a single measurement (up to 3500). A two-dimensional diode array could also be used, for example with a VIPA spectrometer, to acquire massively parallel ringdown signals using the sampling method described in FIG. 4.

What is claimed is:

1. A method of performing cavity enhanced spectroscopy on a test sample on many channels of data at once comprising the steps of:
    (a) providing a high finesse, low-dispersion optical cavity within which the test sample is located;
    (b) coupling a broadband optical frequency comb to the high finesse optical cavity;
    (c) measuring cavity transmission of the high finesse optical cavity at a multiplicity of frequencies;
    (d) determining absorption at the multiplicity of frequencies from the measured cavity transmission at the multiplicity of frequencies.

2. The method of claim 1, further comprising the step of determining the composition of the test sample based upon the absorption at the multiplicity of frequencies.

3. The method of claim 1 wherein the coupling step includes the following steps:
    (b1) measuring the wavelength dependent frequency spacing of cavity modes due to dispersion; and
    (b2) making adjustments based on the wavelength dependent frequency spacing of cavity modes in order to match comb frequencies to cavity modes.

4. The method of claim 3 wherein step b1 includes the steps of detuning the frequency comb from the cavity modes, varying the repetition rate, and monitoring the spectrum of light transmitted from the cavity.

5. The method of claim 3 wherein the step of making adjustments includes the steps of varying the repetition rate and offset of the comb.

6. The method of claim 3 wherein the step of making adjustments includes the steps of adjusting the cavity length and varying at least one of either the sample composition or the sample pressure.

7. The method of claim 3 wherein the step of making adjustments includes the step of maintaining a match between the comb frequencies and the cavity modes using an electronic servo.

8. The method of claim 1 wherein the step of measuring cavity Transmission includes the steps of:
    (c1) spatially separating wavelengths in the transmission; and
    (c2) detecting the intensity at the wavelengths in parallel with a photodiode array and generating voltages based upon the detected intensities.

9. The method of claim 8, wherein the method is performed in a ringdown mode such that the optical frequency comb is interrupted periodically and the cavity transmission is allowed to ring down, and wherein step c2 further includes the steps of comparing the generated voltages over time to a series of descending voltage thresholds, wherein the voltage thresholds are exponentially spaced in order to reduce computations needed to determine decay rate at the wavelengths.

10. The method of claim 1 wherein the step of measuring cavity transmission includes the steps of:
    (c1) sweeping the comb frequencies over a preselected period of time such that a selected group of comb frequencies at a time couple to the cavity; and
    (c2) measuring the intensity of each transmitted group of comb frequencies in turn.

11. The method of claim 10 wherein the selected group of comb frequencies comprises between 1 and 10,000 comb frequencies.

12. Apparatus for performing enhanced spectroscopy on a test sample on many channels of data at once comprising:
   means for providing a broadband optical frequency comb;
   a high finesse, low-dispersion optical cavity within which the test sample is stored;
   means for coupling the optical frequency comb to the cavity, and
   means for measuring cavity transmission at a multiplicity of frequencies.

13. The apparatus of claim 12, further comprising a processor for determining absorption within the cavity at the multiplicity of frequencies from the measured cavity transmission and for determining the composition of the test sample based upon the determined absorption.

14. The apparatus of claim 12 wherein the means for coupling comprises:
   means for measuring the wavelength dependent frequency spacing of cavity modes due to dispersion; and
   means for making adjustments based on the wavelength dependent frequency spacing of cavity modes in order to match comb frequencies to cavity modes.

15. The apparatus of claim 14 wherein the means for measuring comprises means for detuning the frequency comb from the cavity modes, means for varying the repetition rate, and means for monitoring the spectrum of light transmitted from the cavity.

16. The apparatus of claim 14 wherein the means for making adjustments varies the repetition rate and offset of the comb.

17. The apparatus of claim 14 wherein the means for making adjustments adjusts the cavity length and varies at least one of either the sample composition or the sample pressure.

18. The apparatus of claim 14 wherein the means for making adjustments includes an electronic servo for maintaining the match between comb frequencies and cavity modes.

19. The apparatus of claim 12 wherein the means for measuring cavity transmission comprises:
   an element for spatially separating wavelengths in the transmission; and
   a photodiode array configured to detect the intensities of separated wavelengths and generate voltages based upon the detected intensities.

20. The apparatus of claim 19 configured to operate in ringdown mode and further comprising:
   means for interrupting the optical frequency comb periodically; and
   means for comparing the generated voltages over time to a series of descending voltage thresholds, wherein the voltage thresholds are exponentially spaced in order to reduce computations needed to determine decay rate at the wavelengths.

21. The apparatus of claim 12 wherein the means for measuring cavity transmission comprises:
   means for sweeping the comb frequencies over a preselected period of time such that a selected group of comb frequencies at a time couples to the cavity; and
   means for measuring the intensity of each transmitted selected group of comb frequencies in turn.

22. The apparatus of claim 21 wherein the selected group of comb frequencies comprises between 1 and 10,000 comb frequencies.

23. The apparatus of claim 12 wherein the means for measuring cavity transmission includes an optical detector.

24. The apparatus of claim 12 wherein the means for providing a broadband optical frequency comb is a mode locked laser.

* * * * *